US010993611B2

(12) United States Patent
Mosaed et al.

(10) Patent No.: US 10,993,611 B2
(45) Date of Patent: May 4, 2021

(54) DEVICE, SYSTEM AND METHOD FOR FUNCTIONAL IMAGING OF EPISCLERAL VESSELS

(71) Applicant: The Regents of the University of California, Oakland, CA (US)

(72) Inventors: Sameh Mosaed, Laguna Hills, CA (US); Ken Lin, Irvine, CA (US)

(73) Assignee: The Regents of the University of California, Oakland, CA (US)

(*) Notice: Subject to any disclaimer, the term of this patent is extended or adjusted under 35 U.S.C. 154(b) by 302 days.

(21) Appl. No.: 15/044,833

(22) Filed: Feb. 16, 2016

(65) Prior Publication Data

US 2016/0262606 A1    Sep. 15, 2016

Related U.S. Application Data

(60) Provisional application No. 62/115,991, filed on Feb. 13, 2015.

(51) Int. Cl.
| | | |
|---|---|---|
| *A61B 3/00* | (2006.01) | |
| *A61B 3/14* | (2006.01) | |
| *A61F 9/007* | (2006.01) | |
| *A61B 3/117* | (2006.01) | |
| *A61B 3/10* | (2006.01) | |

(52) U.S. Cl.
CPC .......... *A61B 3/0025* (2013.01); *A61B 3/0041* (2013.01); *A61B 3/10* (2013.01); *A61B 3/117* (2013.01); *A61B 3/14* (2013.01); *A61F 9/007* (2013.01); *A61F 9/00736* (2013.01); *A61F 9/00781* (2013.01)

(58) Field of Classification Search
None
See application file for complete search history.

(56) References Cited

U.S. PATENT DOCUMENTS

| | | | |
|---|---|---|---|
| 5,377,686 | A | 1/1995 | O'Rourke et al. |
| 7,785,321 | B2 | 8/2010 | Baerveldt et al. |
| 2001/0053873 | A1 | 12/2001 | Schaaf et al. |
| 2003/0232015 | A1 | 12/2003 | Brown et al. |
| 2006/0032507 | A1 | 2/2006 | Tu |
| 2006/0155192 | A1* | 7/2006 | Bendiksen ............. A61B 8/065 600/458 |
| 2006/0253111 | A1* | 11/2006 | Van Valen .......... A61F 9/00806 606/5 |

(Continued)

FOREIGN PATENT DOCUMENTS

| | | |
|---|---|---|
| WO | WO2001/041685 A | 6/2001 |
| WO | WO2013/112700 A1 | 8/2013 |

OTHER PUBLICATIONS

Francis et al., "Morphometric Analysis of Aqueous Humor Outflow Structures with Spectral-Domain Optical Coherence Tomography", Invest. Ophthalmol. Vis. Sci.; 53: 5198-5207.*

(Continued)

*Primary Examiner* — Yi-Shan Yang
(74) *Attorney, Agent, or Firm* — Robert D. Buyan; Stout, Uxa & Buyan, LLP

(57) ABSTRACT

Methods and systems for assessing regional variations in aqueous outflow vessels of the eye and for optimizing locations within the eye stent implantation or other surgical procedures intended to increase aqueous outflow and reduce intraocular pressure.

12 Claims, 11 Drawing Sheets

(56) References Cited

U.S. PATENT DOCUMENTS

| | | | |
|---|---|---|---|
| 2008/0212026 A1* | 9/2008 | Molnar | A61B 3/14 351/206 |
| 2011/0213300 A1 | 9/2011 | McWeeney et al. | |
| 2011/0282190 A1* | 11/2011 | Caffey | A61B 1/00087 600/427 |
| 2012/0277579 A1* | 11/2012 | Sharma | A61B 3/102 600/425 |
| 2013/0058533 A1 | 3/2013 | Ren et al. | |
| 2013/0253402 A1 | 9/2013 | Badawi et al. | |
| 2014/0257075 A1 | 9/2014 | Kagemann et al. | |
| 2014/0354951 A1 | 12/2014 | Izatt et al. | |

OTHER PUBLICATIONS

Lin et al., "In Vivo Quantitative Microvasculature Phenotype Imaging of Healthy and Malignant Tissues Using a Fiber-Optic Confocal Laser Microprobe", Translational Oncology, 2008, vol. 1, No. 2, pp. 84-94.*

ImageJ/Fiji, "Advanced digital microscopy core facility", 2014.*

Grulkowski et al., "Imaging limbal and scleral vasculature using swept source optical coherence tomography", Photonics Letters of Poland 3, No. 4, 2011.*

Becker et al., "optimal fluorescein dose for intravenous application in miniprobe-based confocal laser scanning microscopy in pigs", J. Biophotonics 4, No. 1-2, 108-113 (2011).*

Korb et al., "An evaluation of the efficacy offluorscein, rose bengal, lissamine green, and a new dye mixture for ocular surface staining", Eye & Contact Lens 34(1): 61-64, 2008.*

Wallace et al., "the safety of intravenous fluorescein for confocal laser endomicroscopy in the gastrointestinal tract", Alimentary Pharmacology & Therapeutics, 2010, 31,548-5552.*

Weber et al., "The microvascular system of the striate and extrastriate visual cortex of the macaque", Cerebral Cortex, 2008; 18:2318-2330.*

Freeman et al., "Simultaneous Indocyanine Green and Fluorescein Angiography Using a Confocal Scanning Laser Ophthalmoscope", Arch Ophthalmol. 1998; 116:455-463. (Year: 1998).*

Quigley et al., "The number of people with glaucoma worldwide in 2010 and 2020". Br J Ophthamol. 2006. 90:262-267.

Gedde et al., "Postoperative Complications in the Tube Versus Trabeculectomy (TVT) Study During Five Years of Follow-up". Am J Ophthalmol. May 2012. 153(5):804-814.

Kaplowitz et al., "Techniques and Outcomes of Minimally-Invasive trabecular Ablation and Bypass Surgery". Br J Ophthalmol. May 2014. 98(5):579-585.

Mosaed et al., "Comparative Outcomes between Newer and Older Surgeries for Glaucoma". Trans Am Ophthalmol Soc. 2009. 107:127-135.

Arriola-Villalobos et al., "Combined iStent trabecular micro-bypass stent implantation and phacoemulsification for coexistent open-angle glaucoma and cataract: a long-term study". Br J Ophthalmol. May 2012. 96(5):645-649.

Voskanyan et al., "Prospective, unmasked evaluation of the iStent inject system for open-angle glaucoma: synergy trial". Adv Ther. Feb. 2014. 31(2):189-201.

Francis et al., "Mophometric analysis of aqueous humor outflow structures with spectral-domain optical coherence tomography". Invest Ophthalmol Vis Sci. Aug. 7, 2012. 53(9):5198-5207.

Kagemann et al., "Visualization of the Conventional Outflow Pathway in the Living Human Eye". Ophthalmology. Aug. 2012. 119(8)1563-1568.

Loewen et al., "There has to be a better way evolution of internal filtration glaucoma surgeries". Br J Ophthalmol. Oct. 2013. 97(10):1228-1229.

Brubaker, "Determination of Episcleral Venous Pressure in the Eye: A Comparison of Three Methods". Arch Ophthalmol. 1967. 77(1):110-114.

Sit et al., "Measurement of episcleral venous pressure". Experimental Eye Research. Sep. 2011. 93(3):291-298.

Hann et al., "Imaging the Human Aqueous Humor Outflow Pathway in Human Eyes by Three Dimensional Micro-Computed Tomography (3D micro-CT)". Exp Eye Res. Feb. 2011. 92(2):104-111.

McKee et al., "Anterior Chamber Angle Imaging With Swept-Source Optical Coherence Tomography: Detecting the Scleral Spur, Schwalbe's Line, and Schlemm's Canal". J Glaucoma. Aug. 2013. 22(6):468-472.

Ren et al., "Ex Vivo Optical Coherence Tomography Imaging of Collector Channels with a Scanning Endoscopic Probe". Invest Ophthalmol Vis Sci. 2011. 52(7):3921-3925.

Jacobi et al. "Microendoscopic trabecular surgery in glaucoma management" Ophthalmology, 1999, vol. 106, No. 3 pp. 538-544.

Martin Uram, "Ophthalmic Laser Microendoscope endophotocoagulation" Ophthalmology, 1992, vol. 99, No. 12, pp. 1829-1832.

Office Action dated Mar. 20, 2018 in corresponding Australian Patent Application No. 2016218984.

Extended European Search Report dated Nov. 6, 2018 in related European Application No. 16750071.9.

Hong Jiang et al., "Automated Segmentation and Fractal Analysis of High-Resolution Non-Invasive Capillary Perfusion Maps of the Human Retina," Microvascular Research, vol. 89, Sep. 2013, pp. 172-75.

Lin, Ken Young et al., "In Vivo Quantitative Microvasculature Phenotype Imaging of Healthy and Malignant Tissues Using a Fiber-Optic Confocal Laser Microprobe," Translational Oncology, vol. 1, No. 2, Jul. 2008, pp. 84-94.

Office Action dated Dec. 17, 2019 in corresponding Japanese Patent Application No. 2017-542146.

Freeman, William R., et al., "Simultaneous Indocyanine Green and Fluorescein Angiography Using a Confocal Scanning Laser Ophthalmoscope," Arch. Ophthalmol., 998; 116:455-463.

Office Action dated May 26, 2020 in corresponding Australian Patent Application No. 2019201934.

Drobnjak, D, et al., "Retinal Vessel Diameters and Their Relationship with Cardiovascular Risk and All-Cause Mortality in the Inter99 Eye Study: A 15-Year Follow-Up," Journal of Ophthalmology, vol. 2016, Article ID 6138659, 8 pages, http://dx.doi.org/10.1155/2016/6138659 (2016).

Lusthaus, J.A., et al., "Aqueous Outflow Imaging Techniques and What They Tell Us About Intraocular Pressure Regulation," Eye; https://doi.org/10.1038/s41433-020-01136-y (2020).

* cited by examiner

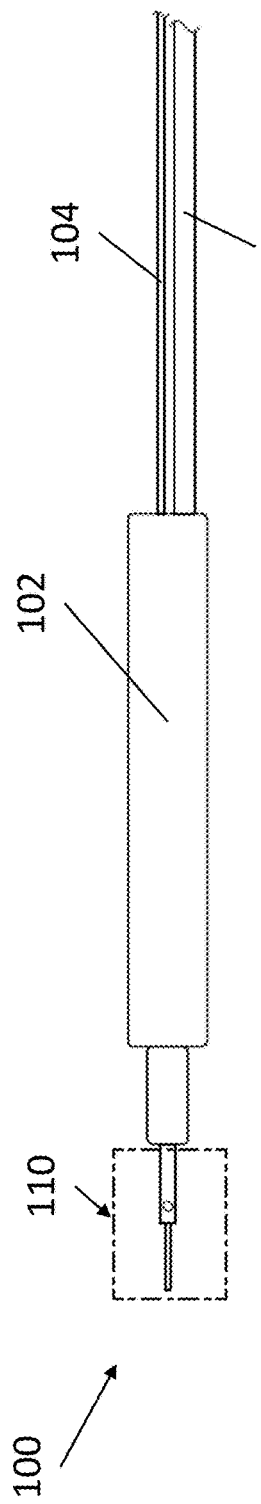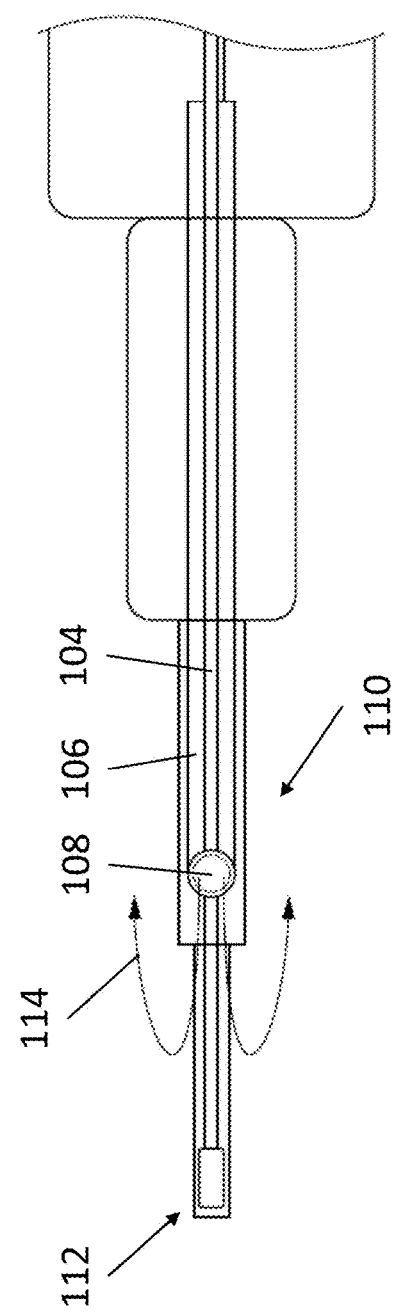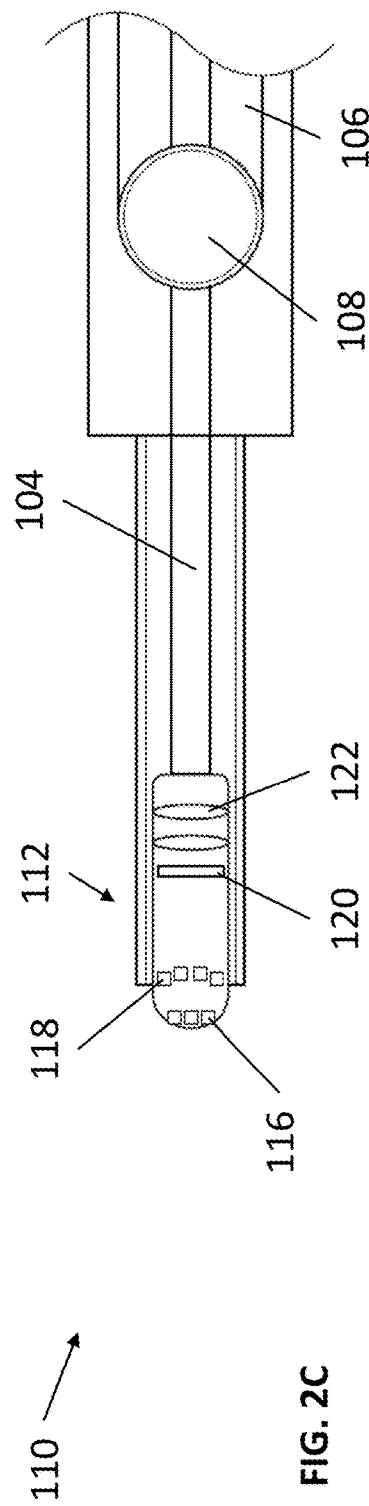

DEVICE, SYSTEM AND METHOD FOR FUNCTIONAL IMAGING OF EPISCLERAL VESSELS

CROSS-REFERENCE TO RELATED APPLICATIONS

This application claims priority to U.S. Provisional Patent Application No. 62/115,991, filed Feb. 13, 2015, the contents of which are incorporated by reference herein in its entirety.

BACKGROUND OF THE INVENTION

The last few years have witnessed rapidly rising interests in both developing new and modifying current Minimally Invasive Glaucoma Surgeries (MIGS). This surge in momentum is no doubt spurred by the fact that the current standard glaucoma surgeries, trabeculectomy and tube shunt surgery, still have high complication rates ranging from 27% of tube shunts to 74% of trabeculectomy (Quigley, H. A. and A. T. Broman, The number of people with glaucoma worldwide in 2010 and 2020. Br J Ophthalmol, 2006. 90(3): p. 262-7; and Gedde, S. J., et al., Postoperative complications in the Tube Versus Trabeculectomy (TVT) study during five years of follow-up. Am J Ophthalmol, 2012. 153(5): p. 804-814.e1). MIGS devices improve the pressure-dependent outflow track by bypassing or ablating the trabecular meshwork (TM), or creating new drainage routes into the suprachoroidal space (Kaplowitz, K., J. S. Schuman, and N. A. Loewen, Techniques and outcomes of minimally invasive trabecular ablation and bypass surgery. Br J Ophthalmol, 2014. 98(5): p. 579-85). Clinical studies so far show MIGS with improved safety profiles, and the most serious complications are temporary hyphema and intraocular pressure (IOP) rise in early postoperative period occurring in 3-10% of trabectome (Mosaed, S., L. Dustin, and D. S. Minckler, Comparative outcomes between newer and older surgeries for glaucoma. Trans Am Ophthalmol Soc, 2009. 107: p. 127-33) and 2% of iStent® patients (Arriola-Villalobos, P., et al., Combined iStent trabecular micro-bypass stent implantation and phacoemulsification for coexistent open-angle glaucoma and cataract: a long-term study. Br J Ophthalmol, 2012. 96(5): p. 645-9; and Voskanyan, L., et al., Prospective, unmasked evaluation of the iStent® inject system for open-angle glaucoma: synergy trial. Adv Ther, 2014. 31(2): p. 189-201).

IOP reduction in MIGS is generally not as dramatic as seen in trabeculectomies and tube shunts, which are the gold standard for glaucoma surgical management. Clinical studies show an average 15.2 mmHg for phaco-trabectome at 5 years, and 16.8 mmHg for the iStent with phacoemulsification at 5 years (Mosaed et al., Arriola-Villalobos et al., and Voskanyan et al.). Since the ablative type MIGS such as trabectome are capable of removing a large arc of TM, they can generally achieve lower IOP endpoints compared to the bypass type such as iStent (Kaplowitz et al.). However, this comes at an expense of higher rate of transient postoperative IOP rise and hyphema. Furthermore, anatomic studies have shown that Schlemm's canals are highly segmented and discontinuous, and the location and number of the collector channels vary among individuals (Francis, A. W., et al., Morphometric analysis of aqueous humor outflow structures with spectral-domain optical coherence tomography. Invest Ophthalmol Vis Sci, 2012. 53(9): p. 5198-207; and Kagemann, L., et al., Visualization of the conventional outflow pathway in the living human eye. Ophthalmology, 2012. 119(8): p. 1563-8). Bypassing an area of TM far away from the collector channels may thus not achieve the full potential of IOP reduction. These lines of evidence all suggest that the real estate value of the TM is not the same across the entire 12 clock hours. In other words, knowing what segment of the TM to ablate or bypass may be crucial to achieve more targeted MIGS and potentially narrow the gap between the IOP endpoints currently seen in MIGS and the theoretical limit of the episcleral venous pressure (Loewen, N. A. and J. S. Schuman, There has to be a better way: evolution of internal filtration glaucoma surgeries, in Br J Ophthalmol. 2013: England. p. 1228-9; Brubaker, R. F., Determination of episcleral venous pressure in the eye. A comparison of three methods. Arch Ophthalmol, 1967. 77(1): p. 110-4; and Sit, A. J. and J. W. McLaren, Measurement of episcleral venous pressure. Exp Eye Res, 2011. 93(3): p. 291-8).

One intuitive approach to target the high-yield TM is to identify the collector channels via imaging (Loewen et al.). Several studies have successfully imaged the outflow anatomy using 3D-micro computed tomography (Hann, C. R., et al., Imaging the aqueous humor outflow pathway in human eyes by three-dimensional micro-computed tomography (3D micro-CT). Exp Eye Res, 2011. 92(2): p. 104-11), swept-source optical coherence tomography (ss-OCT) (McKee, H., et al., Anterior chamber angle imaging with swept-source optical coherence tomography: detecting the scleral spur, Schwalbe's Line, and Schlemm's Canal. J Glaucoma, 2013. 22(6): p. 468-72), and endoscopic OCT (Ren, J., et al., Ex vivo optical coherence tomography imaging of collector channels with a scanning endoscopic probe. Invest Ophthalmol Vis Sci, 2011. 52(7): p. 3921-5). One group has shown the angle structure using swept source OCT while another group has shown the intrascleral plexus using micro-CT. Micro-CT has shown, in great details, the complexity of intra- and episcleral vessels, however, this imaging modality is limited to ex vivo settings. Further, these studies share in common that they all require extensive tissue processing which limits the clinical applicability. While swept source OCT has great clinical translatability, image acquisition of the entire 360 degree may require up to several seconds, which can be confounded by motion artifacts. In addition, several studies have shown that Schlemm's canal can partially collapse under increased IOP. This can make consistent identification of the angle structures more challenging. Lastly, OCT provides ample anatomical data, but the functional correlations to guide the locations for MIGS procedure are currently still lacking. A new technique is needed to help highlight the lumen of the outflow pathway. An intraoperative technique has recently been proposed to locate larger-caliber aqueous veins by observing episcleral venous fluid wave. This technique is obviously limited to intraoperative use, and it is largely a qualitative and subjective method.

What is needed is a device, system, and method utilizing a microendoscope that is capable of detecting episcleral vessels. Further, there is a desire to detect and quantify regional differences in episcleral vessel morphology across the 12 clock hours of the lim bus. A method is also needed to identify, preoperatively and noninvasively, areas of TM that MIGS procedures should access to yield the lowest post-operative IOP possible. Such systems and methods should be functional in real-time, and not require delays for extensive tissue image processing.

SUMMARY OF THE INVENTION

In certain aspects, the invention involves a microendoscope device capable of quantifying the collector channels of an eye using an ab-interno (imaging from within the eye) approach or an ab-externo approach. The invention also involves the use of a microendoscope with a width of about 1.5 mm. The drainage pathway from the inside to the outside of the eye is best seen if a contrast agent is injected into the eye and as the contrast agent exits the eye, it would then go through the functional portion of the outflow pathway and delineate it. The microendoscope is then placed on the conjunctiva of the eye near the limbus to measure the density and diameter of the vessels around the eye's limbal perimeter. The area with more vessel density and diameter would indicate greater flow in that area. This functional information can then guide the surgeon to perform MIGS procedures, which should be targeted to areas with high flow.

In one aspect, the invention is a method for imaging episcleral vessels in an eye including the steps of injecting the eye with a contrast fluid, positioning an imaging probe proximate to the trabecular meshwork including the limbus, acquiring a plurality of images along a circumference of the limbus, and applying a vessel segmentation algorithm to the plurality of images to quantify episcleral diameter and density in real-time.

In another aspect, the invention is a method for quantifying regional flow variation along a circumference of a limbus in an eye including the steps of injecting the eye with a contrast fluid, positioning an imaging probe proximate to a limbus of the eye, acquiring a plurality of images along the circumference of the limbus, and applying a vessel segmentation algorithm to the plurality of images to quantify regional flow variation in real-time.

In yet another aspect, the invention is a system for imaging episcleral vessels in an eye including a processing unit operably connected to an imaging probe and a visual feedback device. The processing unit is configured to apply a vessel segmentation algorithm to a plurality of images taken along a circumference of limbus of an eye perfused with a contrast fluid, and the processing unit is configured to generate an image in real-time on the visual feedback device based on the vessel segmentation algorithm, the image including a composite image that quantifies episcleral diameter and density.

In yet another aspect, the invention is a microendoscope device for imaging episcleral vessels in an eye. The microendoscope device comprises a handpiece comprising a proximal end, a distal end, and at least one lumen therethrough; an intraocular tip positioned at the distal end of the handpiece, the intraocular tip comprising a distal section having an imaging transducer and a distal section having an irrigation port; at least one cable extending through the at least one lumen of the handpiece, the at least one cable operably connected to the imaging transducer; and at least one irrigation tube extending through the at least one lumen of the handpiece, the irrigation tube connected to the irrigation port. In some embodiments, the imaging transducer comprises at least one forward viewing mirror and at least one side viewing mirror. In some embodiments, the imaging transducer comprises at least one confocal mirror. In some embodiments, the imaging transducer comprises at least one ultrasound transducer. In some embodiments, the intraocular tip is suitably sized for use in an ab-externo or an ab-interno procedure. In some embodiments, the intraocular tip is capable of imaging anatomical structures of the eye. In some embodiments, the anatomical structures of the eye are aqueous drainage structures including Schlemm's canal, septations within Schlemm's canal, and channels downstream from Schlemm's canal.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 2A is an image of an exemplary microendoscope device for imaging episcleral vessels in an eye. FIG. 2B is a magnified view of the intraocular tip of an exemplary microendoscope device. FIG. 2C is a magnified view of the imaging transducer of an exemplary microendoscope device.

DETAILED DESCRIPTION OF THE INVENTION

It is to be understood that the figures and descriptions of the present invention have been simplified to illustrate elements that are relevant for a more clear comprehension of the present invention, while eliminating, for the purpose of clarity, many other elements found in systems and methods of imaging episcleral vessels. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

As demonstrated herein, a microendoscope may be used to visualize episcleral vessels and characterize their density and diameters after intracameral fluorescein injection in an eye with minimal tissue manipulation. The microendoscope thereby allows a clinician to perform a real-time optical biopsy by visualizing microvasculature in tissues as well as detecting abnormal cells.

System

Figure 1:
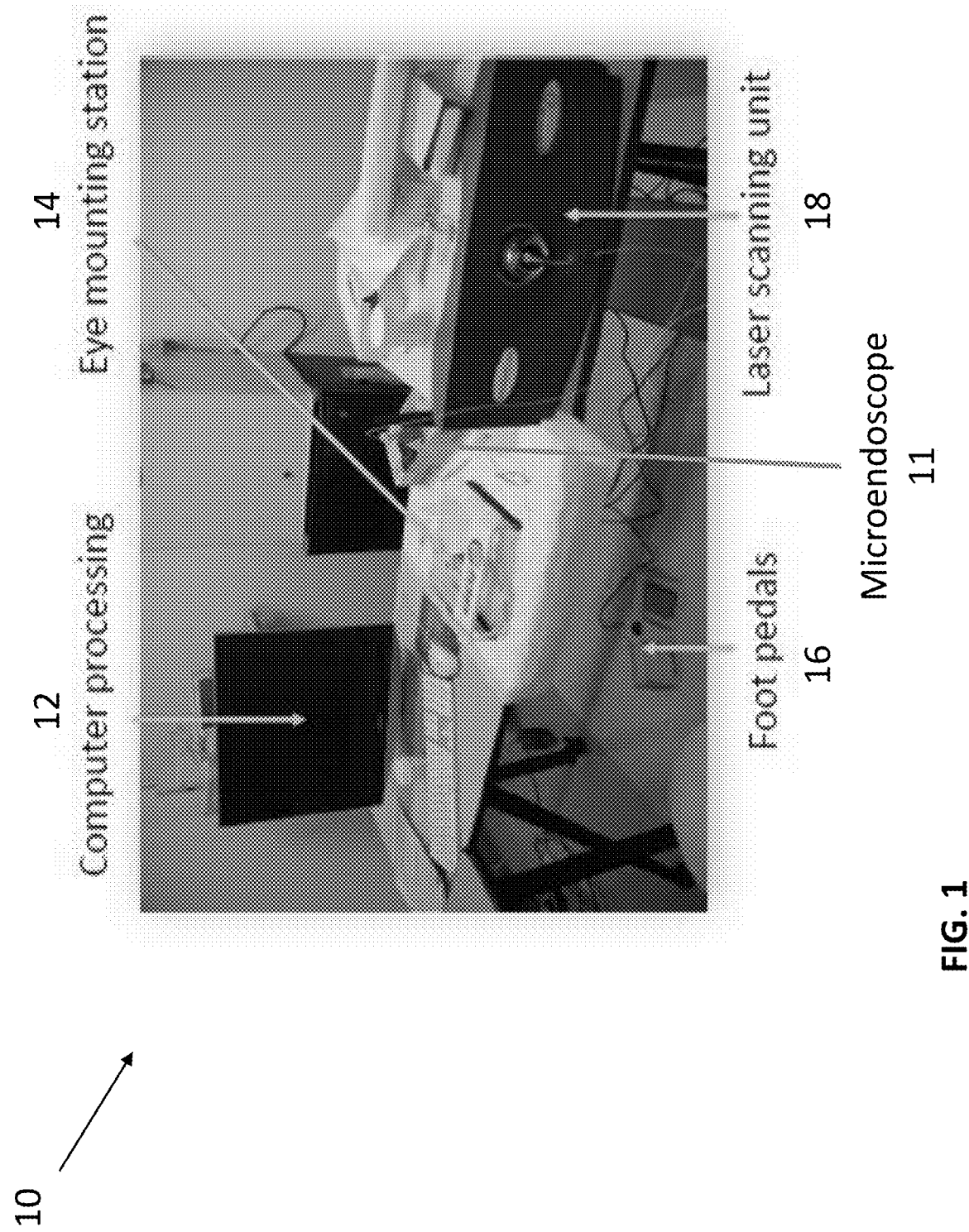
FIG. 1 is an image of an exemplary fiber-optic confocal laser microendoscope imaging system for imaging episcleral vessels in an eye.

Accordingly, the invention includes a system for real-time, functional imaging of episcleral vessels. As shown in FIG. 1, the system 10 generally includes a microendoscope 11, a laser scanning unit 18, foot petals 16 for initiating image acquisition and a computer station 12. In some embodiments, the system further comprises an ultrasound imaging unit (not pictured). The computer station 12 includes at least one processor, standard input and output devices, as well as all hardware and software typically found on computing devices for storing data and running programs, and for sending and receiving data over a network, if needed. Computer station 12 further includes a monitor or other visual display for providing visual user feedback of imaging data. In embodiments comprising a laser scanning unit, a 488-nm laser source may be rastered by two mirrors on one end of a fiber bundle consisting of 30,000 optic fibers. The laser may be sequentially directed into each fiber to reach the tissue. The fluorescent emission is collected back into the same fiber that was used for illumination. The small core diameter of each fiber acts as a pinhole to give the probe optical sectioning capability. The microendoscope is preferably suitable for tissue penetration depths of 30 microns. Additionally, the microendoscope preferably has a diameter of 1.5 mm and projects a field of view of 423 by 423 micron. Lateral and axial resolutions preferably are 3.5 and 15 micron, respectively. A post-processing image frame or video may be shown on the monitor of computer station 12 to allow the surgeons to navigate along the trabecular meshwork, including the limbus, in real-time. Without limitation, an exemplary system suitable for use as described herein is the Cellvizio® system available from Mauna Kea Technologies, Inc.

The computing station 12 of system 10 may also have associated therewith a software platform that may operate as a local or remote executable software platform. As contemplated herein, any other computing device as would be understood by those skilled in the art may be used with the system, including desktop or mobile devices, laptops, tablets, wireless digital/cellular phones, televisions or other thin client devices as would be understood by those skilled in the art.

For example, the computer operable component(s) of the system may reside entirely on a single computing device, or may reside on any number of devices within the system. Similar to computer station 12, any computing devices contemplated herein may generally include at least one processor, standard input and output devices, as well as all hardware and software typically found on computing devices for storing data and running programs, and for sending and receiving data over a network. The computing device(s) may also be connected directly or via a network to remote databases, such as for additional storage backup, and to allow for the communication of files, email, software, and any other data format between two or more computing devices. There are no limitations to the number, type or connectivity of the databases utilized by the system of the present invention.

The system 10 may include a communications network as would be understood by those having ordinary skill in the art, such as, for example, an open, wide area network (e.g., the internet), an electronic network, an optical network, a wireless network, a physically secure network or virtual private network, and any combinations thereof. The communications network may also include any intermediate nodes, such as gateways, routers, bridges, internet service provider networks, public-switched telephone networks, proxy servers, firewalls, and the like, such that the communications network may be suitable for the transmission of information items and other data throughout the system 10.

Further, the communications network may use standard architecture and protocols as understood by those skilled in the art, such as, for example, a packet switched network for transporting information and packets in accordance with a standard transmission control protocol/Internet protocol ("TCP/IP"). Any of the computing devices may be communicatively connected into the communications network through, for example, a traditional telephone service connection using a conventional modem, an integrated services digital network ("ISDN"), a cable connection including a data over cable system interface specification ("DOCSIS") cable modem, a digital subscriber line ("DSL"), a T1 line, or any other mechanism as understood by those skilled in the art. Additionally, the system may utilize any conventional operating platform or combination of platforms (Windows, Mac OS, Unix, Linux, Android, etc.) and may utilize any conventional networking and communications software as would be understood by those skilled in the art.

To protect data, an encryption standard may be used to protect files from unauthorized interception over the network. Any encryption standard or authentication method as may be understood by those having ordinary skill in the art may be used at any point in the system of the present invention. For example, encryption may be accomplished by encrypting an output file by using a Secure Socket Layer (SSL) with dual key encryption. Additionally, the system may limit data manipulation, or information access.

As mentioned previously, the system may include an application software, which may be managed by a local or remote computing device. The software may include a software framework or architecture that optimizes ease of use of at least one existing software platform, and that may also extend the capabilities of at least one existing software platform. The application architecture may approximate the actual way users organize and manage electronic files, and thus may organize use activities in a natural, coherent manner while delivering use activities through a simple, consistent, and intuitive interface within each application and across applications. The architecture may also be reusable, providing plug-in capability to any number of applications, without extensive re-programming, which may enable parties outside of the system to create components that plug into the architecture. Thus, software or portals in the architecture may be extensible and new software or portals may be created for the architecture by any party.

The system may provide software accessible to one or more users to perform one or more functions. Such applications may be available at the same location as the user, or at a location remote from the user. Each application may provide a graphical user interface (GUI) for ease of interaction by the user with information resident in the system. A GUI may be specific to a user, set of users, or type of user, or may be the same for all users or a selected subset of users. The system software may also provide a master GUI set that allows a user to select or interact with GUIs of one or more other applications, or that allows a user to simultaneously access a variety of information otherwise available through any portion of the system.

The system software may also be a portal or SaaS that provides, via the GUI, remote access to and from the system of the present invention. The software may include, for example, a network browser, as well as other standard applications. The software may also include the ability, either automatically based upon a user request in another application, or by a user request, to search, or otherwise retrieve particular data from one or more remote points, such as on the internet or from a limited or restricted database. The software may vary by user type, or may be available to only a certain user type, depending on the needs of the system. Users may have some portions, or all of the application software resident on a local computing device, or may simply have linking mechanisms, as understood by those skilled in the art, to link a computing device to the software running on a central server via the communications network, for example. As such, any device having, or having access to, the software may be capable of uploading, or downloading, any information item or data collection item, or informational files to be associated with such files.

Presentation of data through the software may be in any sort and number of selectable formats. For example, a multi-layer format may be used, wherein additional information is available by viewing successively lower layers of presented information. Such layers may be made available by the use of drop down menus, tabbed folder files, or other layering techniques understood by those skilled in the art or through a novel natural language interface as described herein. Formats may also include AutoFill functionality, wherein data may be filled responsively to the entry of partial data in a particular field by the user. All formats may be in standard readable formats, such as XML. The software may further incorporate standard features typically found in applications, such as, for example, a front or "main" page to present a user with various selectable options for use or organization of information item collection fields.

The system software may also include standard reporting mechanisms, such as generating a printable results report, or an electronic results report that can be transmitted to any communicatively connected computing device, such as a generated email message or file attachment. Likewise, particular results of the aforementioned system can trigger an alert signal, such as the generation of an alert email, text or phone call, to alert a user of the particular results. Further embodiments of such mechanisms are described elsewhere herein or may standard systems understood by those skilled in the art.

The system may further include an injectable fluorescent agent, such as fluorescein, to produce contrast in the target tissue when imaged with the confocal microendoscope. In one embodiment, Fluress™, which contains 0.25% fluorescein, may be used. Alternatively, indocyanine green or fluorescent nanoparticles may be used instead of fluorescein. There is no limitation to the type and concentration of agent or probe used, provided that enough probe is injected to provide suitable contrast in the target tissue when imaged. For example, in certain embodiments, a concentration of between 0.001% and 1% of agent or probe is used. While concentrations above 1% may be used, in some instances a higher concentration may potentially clog the trabecular meshwork, depending on the surface chemistry of the contrast agent selected.

Device

In another aspect, the invention further includes a uniquely designed microendoscope device for the applications and method described herein. As shown in FIG. 2A, an exemplary microendoscope device 100 is provided. The microendoscope device 100 generally includes a handpiece 102, a cable 104, an irrigation tube 106, and an intraocular tip 110. As shown in FIG. 2B, intraocular tip 110 generally further includes an imaging transducer 112 and at least one irrigation port 108.

The handpiece 102 comprises an elongate body having a proximal end, a distal end, and at least one lumen running therethrough. Handpiece 102 can comprise any suitable shape, such as rounded shapes and faceted shapes. The shape of handpiece 102 may be described from the shape of its cross section. For example, when viewed head on, handpiece 102 may have a circular cross section, an ovoid cross section, or a polygonal cross section having three, four, or more sides. Handpiece 102 can have any suitable size. In some embodiments, handpiece 102 can have a length between 5 and 10 cm. In some embodiments, handpiece 102 can have a width between 1 and 3 cm. In some embodiments, handpiece 102 can comprise exterior features for improving grip, such as one or more ridges, grooves, bumps, and the like. Handpiece 102 can comprise any suitable material, including but not limited to plastics and metals.

At least one cable 104 extends through the at least one lumen of handpiece 102. The at least one cable 104 carries the signals sent and acquired by the microendoscope device 100. For example, in some embodiments, cable 104 may carry ultrasound signals. In other embodiments, an optic fiber cable 104 may carry optical signals. In certain embodiments, a plurality of cables are provided for carrying a plurality of signals. In some embodiments, at least one cable 104 may be included to provide power to microendoscope device 100.

Irrigation tube 106 extends through the at least one lumen of handpiece 102. Irrigation tube 106 comprises a lumen suitable for delivering a liquid. For example, irrigation tube 106 may deliver a balanced salt solution to maintain the anterior chamber volume of an eye while the microendoscope device 100 is in use. Irrigation tube 106 terminates into the at least one irrigation port 108 near the distal end of handpiece 102. The at least one irrigation port 108 permits irrigation flow 104 of the liquid delivered through irrigation tube 106. In certain embodiments, irrigation tube 106 is detachable.

Intraocular tip 110 is positioned at the distal end of handpiece 102. In some embodiments, intraocular tip 110 is sized to fit within a microincision in the eye. For example, in some embodiments intraocular tip 110 has a width between 0.1 and 2 mm. In certain embodiments, intraocular tip 110 has a length between 1 and 2 cm. Intraocular tip 110 comprises a proximal section and a distal section. The distal section of intraocular tip 110 comprises irrigation port 108 and houses the distal end of irrigation tube 106. The distal section of intraocular tip 110 houses imaging transducer 112 and the distal end of cable 104.

As shown in FIG. 2C, imaging transducer 112 may further include at least one forward viewing mirror 116, at least one side viewing mirror 118, at least one ultrasound transducer 120, and at least one transducer confocal mirror 122. Imaging transducer 112 sends and receives signals for real-time, functional imaging of episcleral vessels, including but not limited to ultrasound signals and laser optical signals. In some embodiments, imaging transducer 112 is operably connected to the at least one cable 104 for transmitting the sent and received signals.

In certain embodiments, handpiece 102 can be adapted for attachment to existing handpiece systems (such as phacoemulsification handpieces, the Trabectome® handpiece, or the iStent® injector). Existing handpiece systems may comprise irrigation means, wherein the irrigation tube 106 may be optionally detached when the microendoscope device is adapted for use with the existing handpiece systems. The microendoscope device is suitable for any procedure, including ab-interno and ab-externo procedures. The dimensions of the device make it suitable for use in imaging anatomical structures of the eye. In some embodiments, the device is capable of imaging aqueous drainage structures of the eye. For example, the device is capable of imaging Schlemm's canal, septations within Schlemm's canal, channels downstream from Schlemm's canal, and the like.

Methods

The invention further includes a method for imaging episcleral vessels in an eye. In one embodiment, the method includes the steps of injecting the eye with a contrast agent, positioning an imaging probe proximate to the trabecular meshwork of the eye (including the limbus), acquiring a plurality of images along a circumference of the limbus, and applying a vessel segmentation algorithm to the plurality of images to quantify episcleral diameter and density in real-time.

The invention may also include a method for quantifying regional flow variation along a circumference of a limbus in an eye. The method may include the steps of injecting the eye with a contrast agent, positioning an imaging probe proximate to a limbus of the eye, acquiring a plurality of images along the circumference of the limbus, and applying a vessel segmentation algorithm to the plurality of images to quantify regional flow variation in real-time. In certain embodiments, the vessel segmentation algorithm may utilize a diameter and density of imaged episcleral vessels to quantify regional flow variation.

In certain embodiments, the images may be acquired at about 15 degree intervals along the circumference of the limbus. In other embodiments, image acquisition can be performed by gliding the microendoscope along the limbus, to capture every degree of the limbal structure.

In certain embodiments, the microendoscope may be positioned between 0 and about 3 mm behind the limbus to gives the best access to the perilimbal vessels that are of the greatest clinical interest to the surgeon. Preferably, the microendoscope may be positioned about 1 mm behind the limbus.

In certain embodiments, the method may further include the step of creating an incision in the eye for imaging Schlemm's canal. For example, a 3 mm by 3 mm triangular scleral flap may be created with its base at the limbus. It should be appreciated that there is no limitation to the size or geometric shape of the scleral flap. In another example, the scleral flap size may range from 2 mm to 5 mm in the base length, and may be generally rectangular in shape. The incisions may have a 50% to 75% scleral depth, beginning at the posterior extent of the surgical limbus extending toward the apex of the triangle, such that the flap can be lifted so that the blue-gray zone of the limbus is accessible for positioning the microendoscope to image Schlemm's canal. When imaging Schlemm's canal, the image acquisition is preferably initiated immediately after fluorescein injection into the anterior chamber.

In certain embodiments, the step of acquiring images may occur about 7 minutes after injecting the eye with a contrast agent, as the contrast agent appears to reach their maximal signal intensity within this time window. However, it should be appreciated that there is no limitation as to the time frame for acquiring images.

In certain embodiments, the episcleral diameter and density may be displayed in an image on a visual feedback device. For example, the image may be a composite image, with a first indicator representing a vessel centerline and a second indicator representing a vessel border.

As contemplated herein, the aforementioned methods may be used for relieving intraocular pressure in an eye by identifying a target treatment area based on the generated images. For example, a MIGS treatment may be applied to the target treatment area, such as an ablative treatment or a MIGS device implant.

Accordingly, the ex vivo platform and the microendoscope device and system described herein, along with the ability to quantify vessel morphology, may serve a pivotal role in helping MIGS achieving lower post-operative IOP. The invention provides a system and method that represents a significantly and unexpected improvement over the episcleral venous pressure methods traditionally used. In addition, the methods of the invention can be performed prior to the surgery, so that patients who do not have an outflow pathway amenable to MIGS procedures, can be spared the surgery too. In this context, the system and methods not only optimize existing surgical techniques, but may also act as a screen for the patients most likely to respond to such surgeries. Further, the methods also represent a significantly less invasive and more clinically translatable as compared to the use of optical coherence tomography (OCT) or micro-CT. The methods presented herein also have significantly less motion artifact, as it does not require the patient to stay absolutely still during the image acquisition period as would be required in the case of OCT.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out particular embodiments of the present invention, and are not to be construed as limiting in any way the remainder of the disclosure.

An operable imaging system, Cellvizio® (Mauna Kea Technologies, Paris, France) was used to image human episcleral vessels. The system components as used in this example are depicted in FIG. 2. Ten porcine eyes (Alcon) and four human eyes (SightLife) were used. The eyes were injected with 0.04% fluorescein (Fluress™ diluted to 0.04% through serial 1:1 dilution with balanced salt solution (BSS)) and kept under constant infusion with a custom made eye mounting station (FIG. 3).

Figure 3:
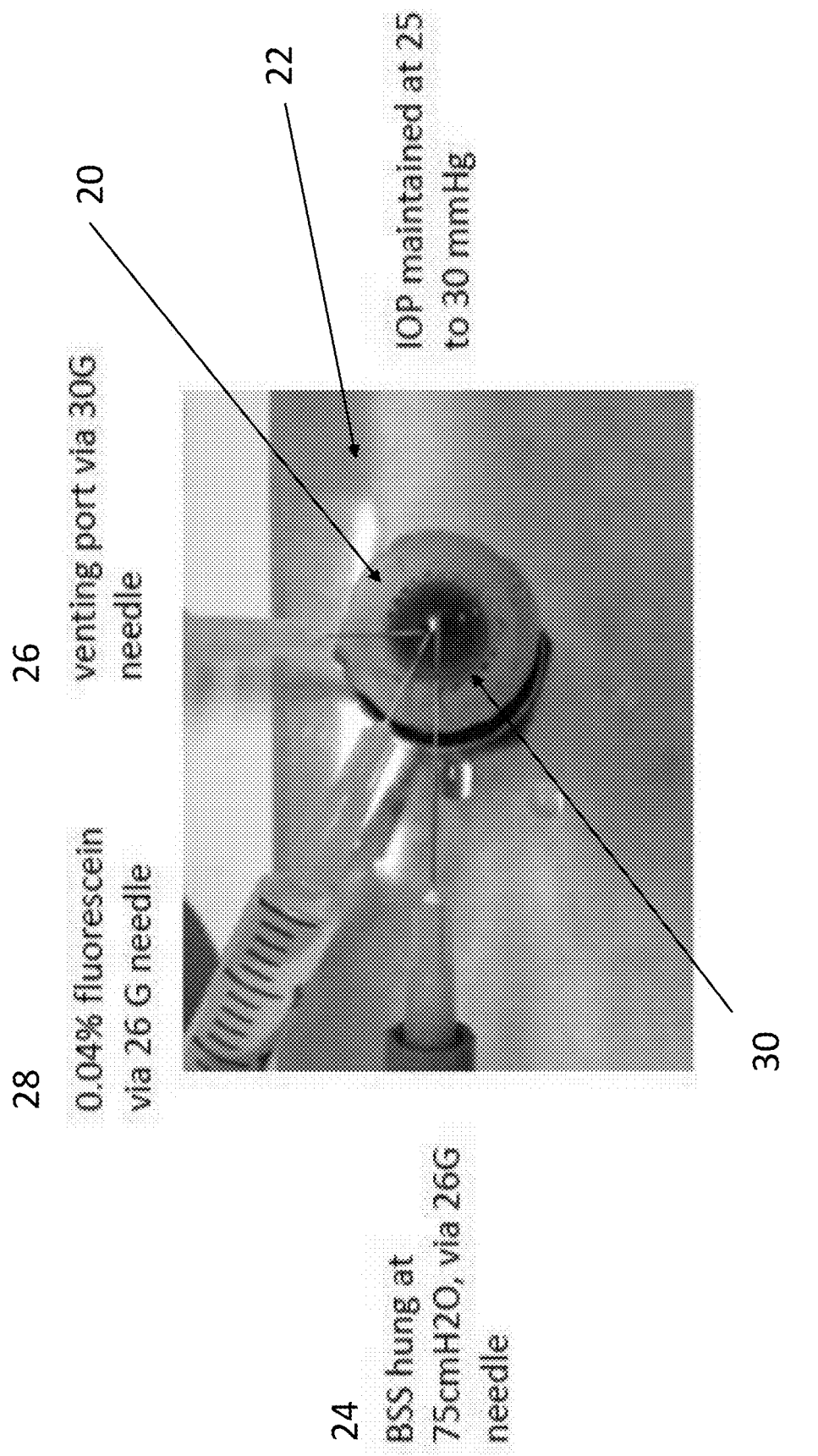
FIG. 3 is an image of an exemplary eye perfusion system.

The porcine eyes were mounted onto a flat platform of the eye mounting station and secured with vacuum suction provided via a syringe, as shown in FIG. 3. The iris plane was made parallel to the ground and confirmed with Axis Assistant, an iPhone-based application. A 360-degree limbal peritomy was performed using mini-Westcott scissors, and the Tenon's tissues were bluntly dissected to expose the bare sclera. With further reference to FIG. 3, BSS solution was hung at 75 cmH2O position and delivered into the eye via a 26 gauge needle (24). This height was chosen as it provides the ex vivo perfused eye platform an IOP of 25 to 30 mm Hg. A smaller-caliber 30 gauge needle (26) was used to create a venting port at 90 degree away from the infusion port. IOP was checked every three minutes by Tonopen. A 26 gauge needle (28) was inserted half-way between the infusion and venting ports to inject 0.2 cc of 0.04% fluorescein over five seconds once the tip of the needle reached a point 1 mm above the center of the anterior lens capsule with a bevel-up position to minimize preferential delivery of fluorescein to a particular quadrant of the angle.

Of the four human eyes, cadaveric human eyes were from a 78-year-old male and an 82-year old male with no history of glaucoma or eye surgery. The eyes from the 82-year-old man were used for the initial study determining optimal image time window after fluorescein injection, while the 78-year-old man's eyes were used for all the subsequent studies. The eye was mounted onto the perfusion platform as described above. The superior pole of the eye was identified based on the relative location of the optic nerve and inferior oblique muscle insertion. Both human eyes had only trace amount of conjunctival and Tenon's tissues and no dissection or tissue manipulation was performed on the human eyes prior to mounting the eyes.

To facilitate visualization of Schlemm's canal, which lies approximately 200 micron underneath the sclera deep beyond the microendoscope's 30 micron penetration depth, a triangular limbal scleral flap was created. Briefly, a no. 69 Beaver blade was used to create a 3 mm by 3 mm triangular scleral flap with its base at the limbus. The blade was used to create two, 50% to 75% scleral depth incisions beginning at the posterior extent of the surgical limbus extending toward the apex of the triangle. Next, the no. 69 Beaver blade was used in an almost horizontal fashion across the apex of the triangle to lift the edge of the flap from the bottom of the grooves. Non-toothed forceps were then used to lift the flap and create traction between the flap and scleral bed. The no. 69 blade was used in a horizontal fashion to cut across the scleral tissue. The dissection was carried anteriorly until the blue-gray zone of the limbus was visible. The microendoscope was then placed above the blue-gray zone to image Schlemm's canal. Image acquisition was initiated immediately after fluorescein injection into the anterior chamber.

To determine the optimal time for imaging (after fluorescein injection), each eye was mounted as previously described, and the microendoscope was gently pressed against the lim bus 180 degree away from the infusion port. Video acquisition was initiated by the surgeon via a foot pedal 16 (e.g. FIG. 1) after completion of the fluorescein injection. The microendoscope was held stationary by the surgeon to maintain the same view and the increase in intraluminal fluorescence was seen in real-time on the monitor for eight minutes. The same protocol was used for both porcine and human eyes. Image analysis was performed using ImageCell (Mauna Kea Technologies, Paris, France). A circular region of interest (ROI) was manually made to match the microendoscope's field of view. The total signal intensity within the ROI at each frame was calculated and plotted against time.

To quantify vessel diameter and fluorescent signal along 360 degree of the limbus, the limbus was marked with a surgical blue marker 30 placed at 15 degree apart. Still images at each mark were acquired at five minutes for the porcine eyes and at seven minutes for human eyes.

A vessel segmentation algorithm was applied to each frame to outline the border of the lumen and compute the vessel diameter in a manner as described and validated previously (Smistad, E., A. C. Elster, and F. Lindseth, GPU accelerated segmentation and centerline extraction of tubular structures from medical images. Int J Comput Assist Radiol Surg, 2014. 9(4): p. 561-75; and Karl, K., Model-Based Detection of Tubular Structures in 3D Images. 2000. 80(2): p. 130-171). Briefly, vessels were modeled as tubular structures with the intraluminal signal intensity having a Gaussian distribution with the signal maxima denoting the luminal center, or "ridge." Given that vessel diameter can have local variation along the direction of the lumen, the ridges are detected at different scales, and the medium response was computed, and the maxima of the response through the scales were kept. The scale at which a maximum ridge was detected led to an estimate of vessel radius. The segmentation algorithm thus generated several sets of connected points, with each set representing a vessel midline and each point within a set carrying an associated diameter information. These points were denoted and overlaid onto the original image to provide a graphical representation of where the vessel borders were. A data table containing vessel diameter information could then be exported to Excel for statistical analysis.

All values were expressed as mean+/−SD. No statistical analysis was performed on the signal rise time after fluorescein injection in three porcine and two human eyes as these were observational experiment aimed to determine the optimal timeframe for data collection in subsequent experiments. For comparison of signal intensity between the inferior quadrants vs. all other quadrants, the signals from the inferior quadrant, defined as 225 degree to 315 degree from two human eyes were compared with signals from all other quadrants. A single-tailed t-test was used to determine statistical significance, whereby a $p<0.05$ denotes significance.

Figure 4:
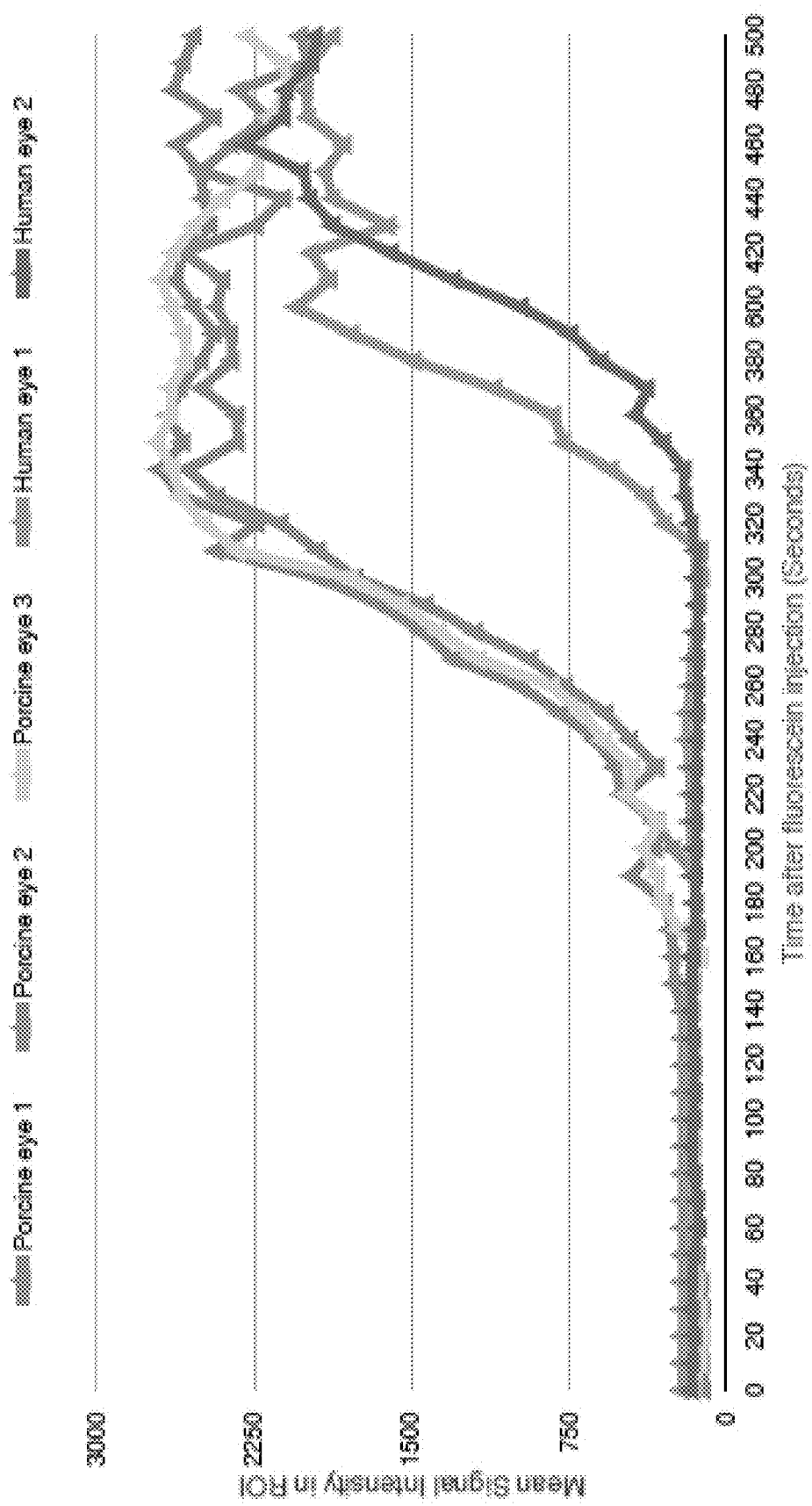
FIG. 4 is graph showing mean signal intensity in the region of interest over time (after fluorescein injection).

Porcine eyes began to reach the plateau phase of the fluorescent signal five minutes after fluorescein injection. For human eyes, the peak time occurred at seven minutes after fluorescein injection. The plot shown in the graph of FIG. 4 shows that the optimal time to capture image is five minutes after injection in porcine eyes and seven minutes after injection in human eyes.

Visualization of episcleral vessels (FIGS. 5A and 5B) and Schlemm's canal (FIGS. 5C and 5D) with minimal tissue manipulation are shown. Episcleral vessels were seen emanating from deeper, larger-caliber vascular structures. The white bar 40 in FIG. 4A represents 50 micron of length. Episcleral vessels with diameter ranging from 10 to 50 microns were seen emanating into the scleral surface (FIGS.

Figure 5B:
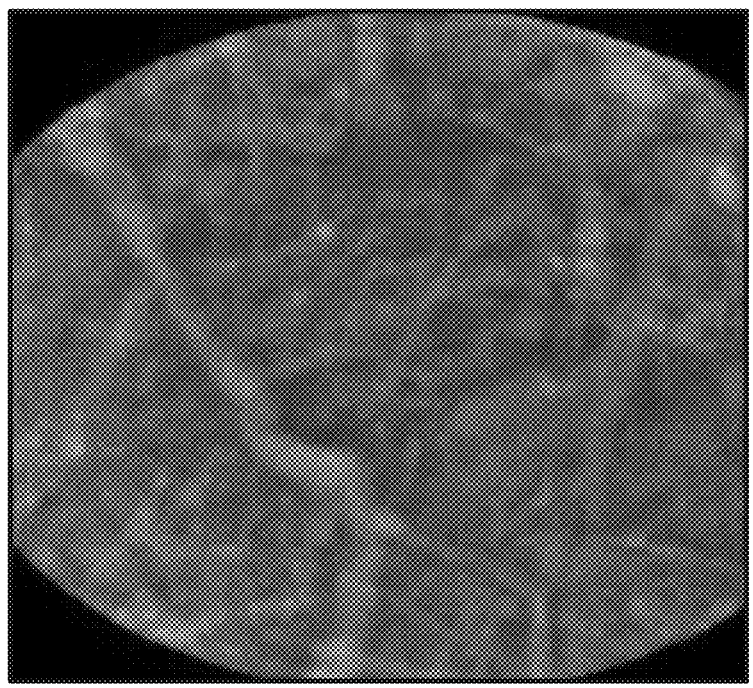
FIGS. 5A and 5B are images of episcleral vessels.
Figure 5A:
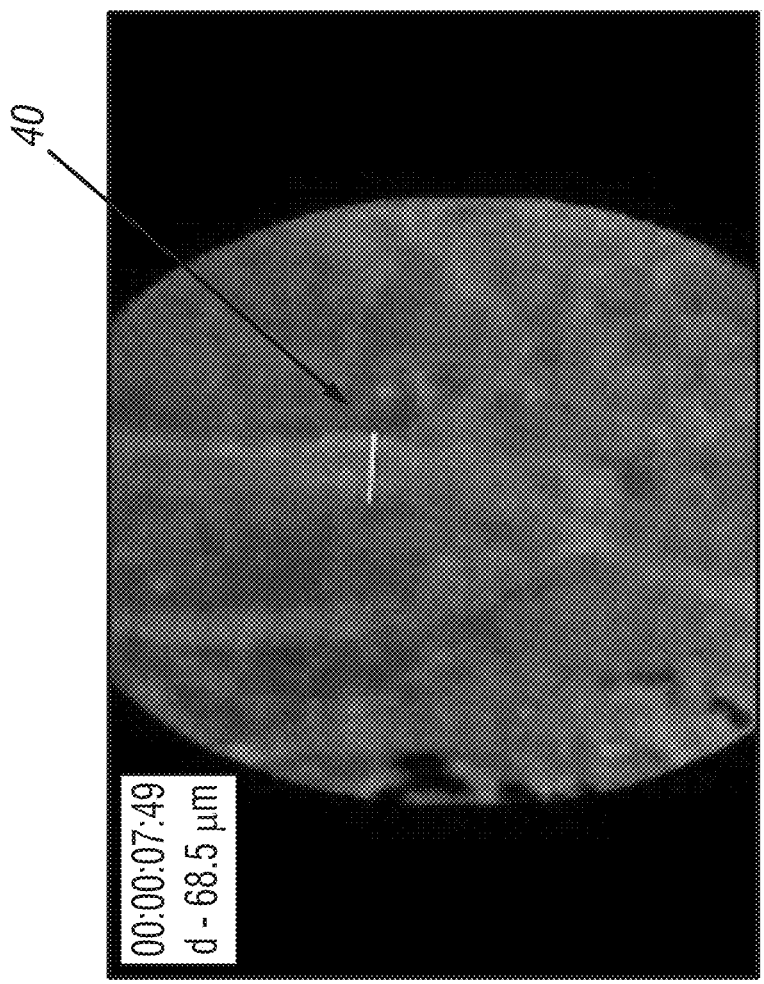
Figure 5D:
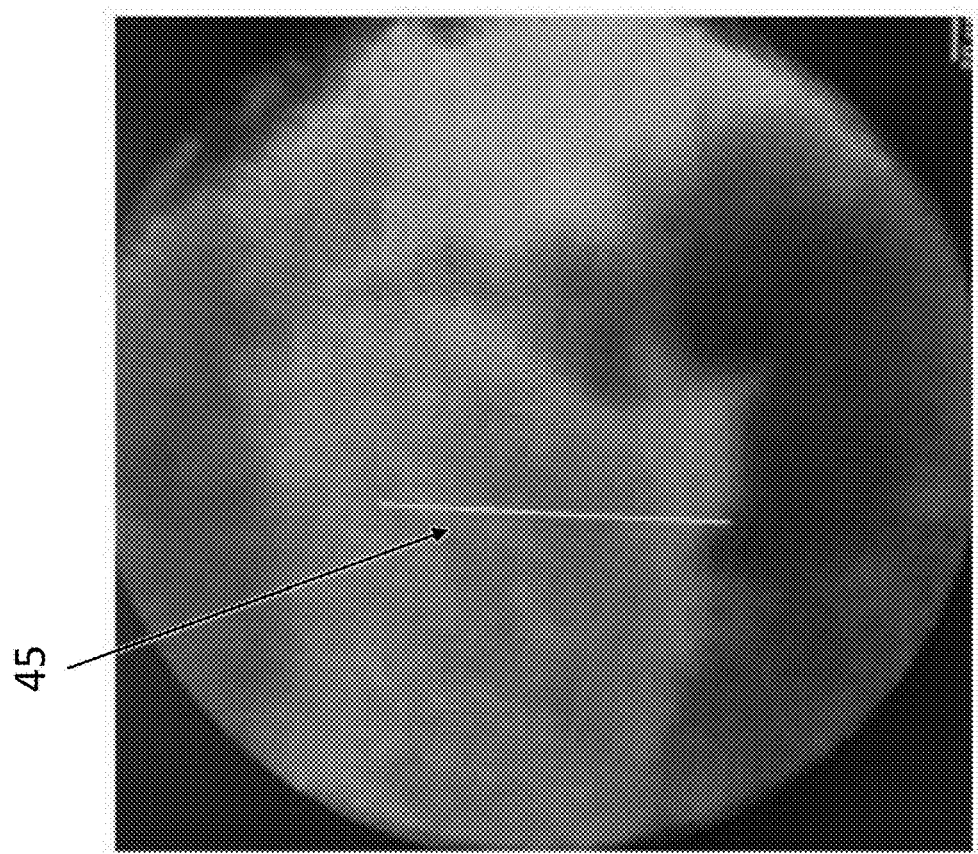
FIGS. 5C and 5D are images of Schlemm's canal.
Figure 5C:
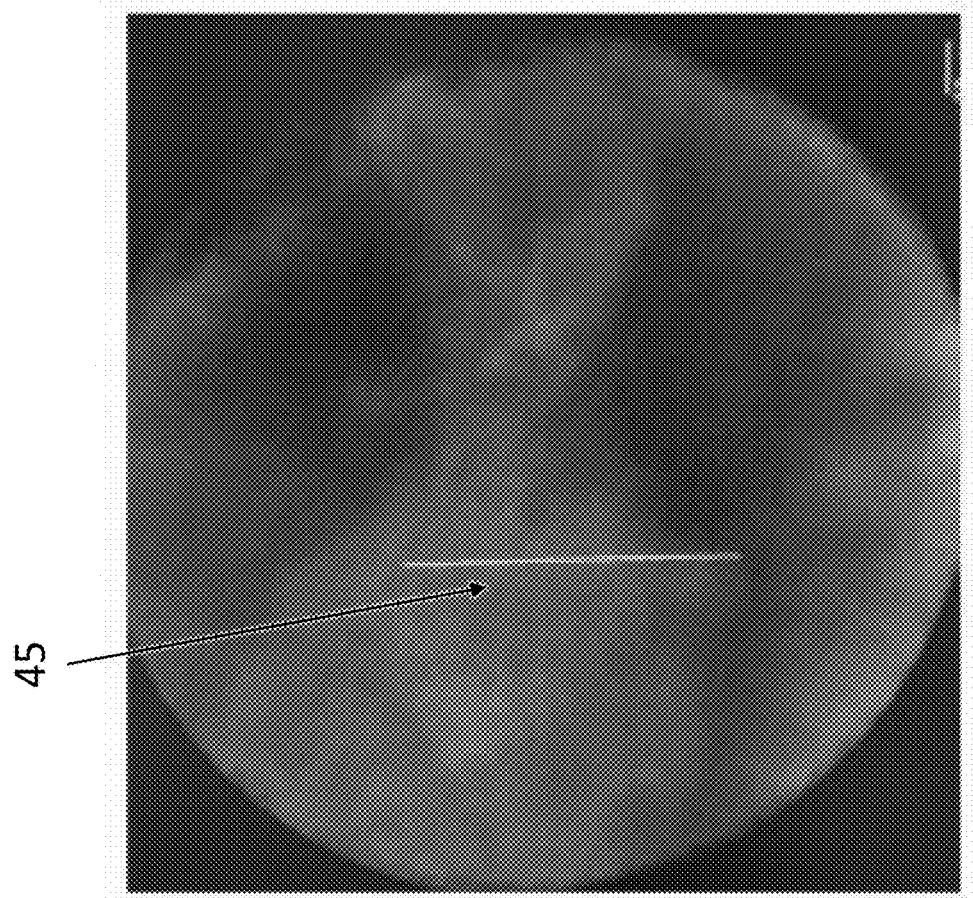

5A and 5B). Visualization of Schlemm's canal is only possible after a scleral flap is made because the microendoscope is limited to a depth of 30 micron in scleral tissue. The white bar 45 in FIGS. 5C and 5D represents a length of 120 micron. Although Schlemm's canal was visualized after creation of a scleral flap, image quality was quickly degraded as fluorescein began to leak through the scleral flap edges. The images shown in FIGS. 5A and 5B were obtained from human eyes without tissue processing.

Figure 6A:
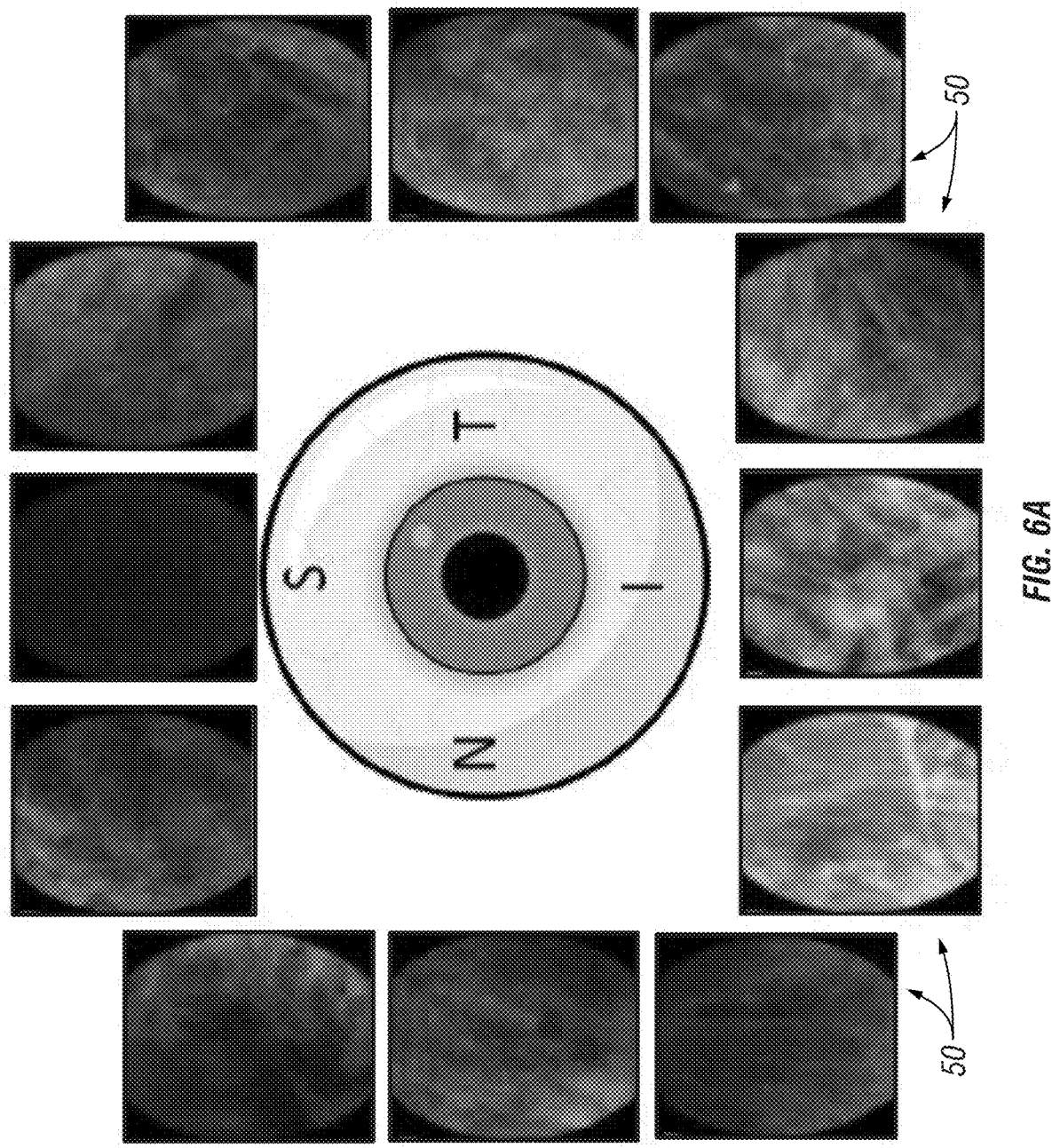
FIG. 6A shows images of distribution of the fluorescence signal along the 12 clock hours of the limbal perimeter.
Figure 6C:
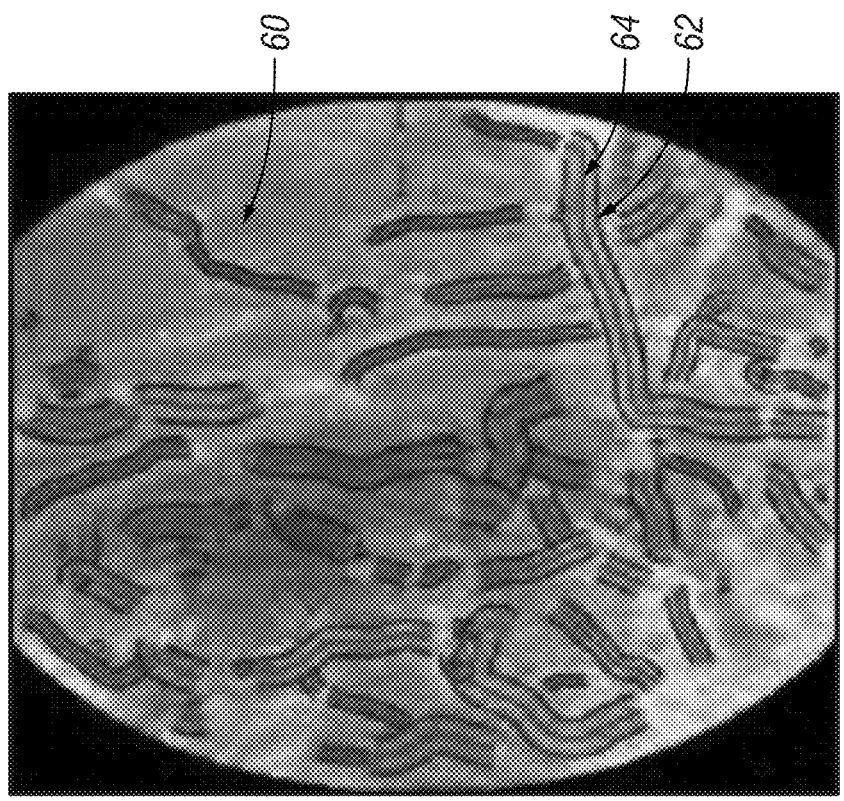
FIGS. 6B and 6C show images quantifying vessel diameter and signal intensity or density in the chosen region of interest.
Figure 6B:
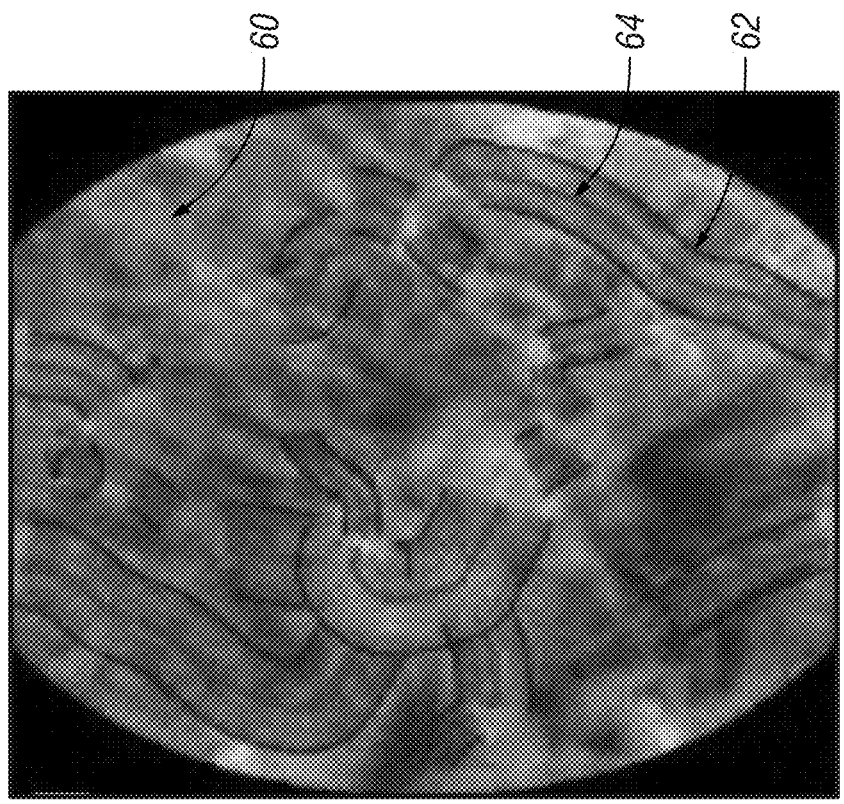
Figure 7:
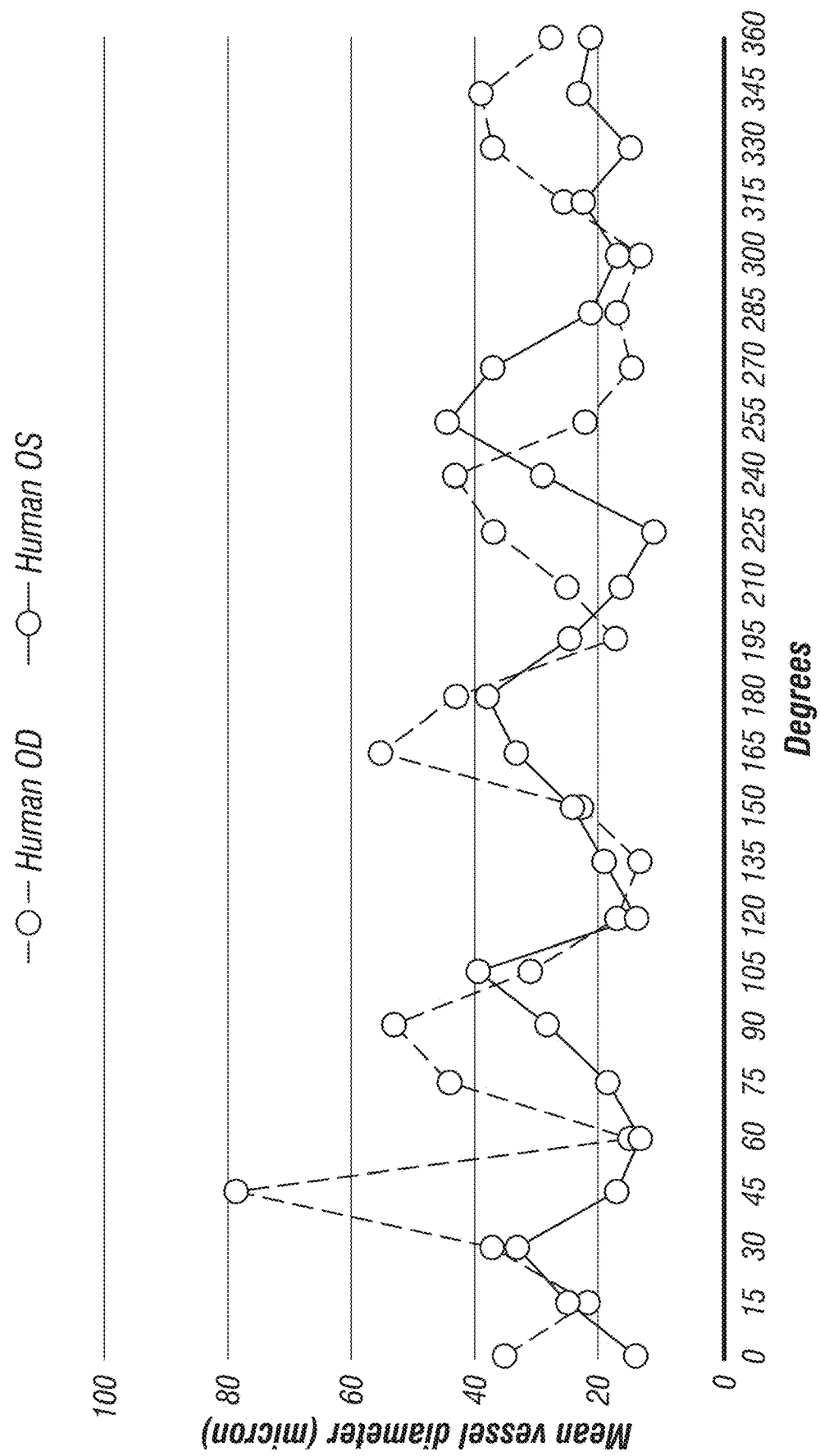
FIG. 7 is a graph showing episcleral diameter distribution along the limbal perimeter.
Figure 8A:
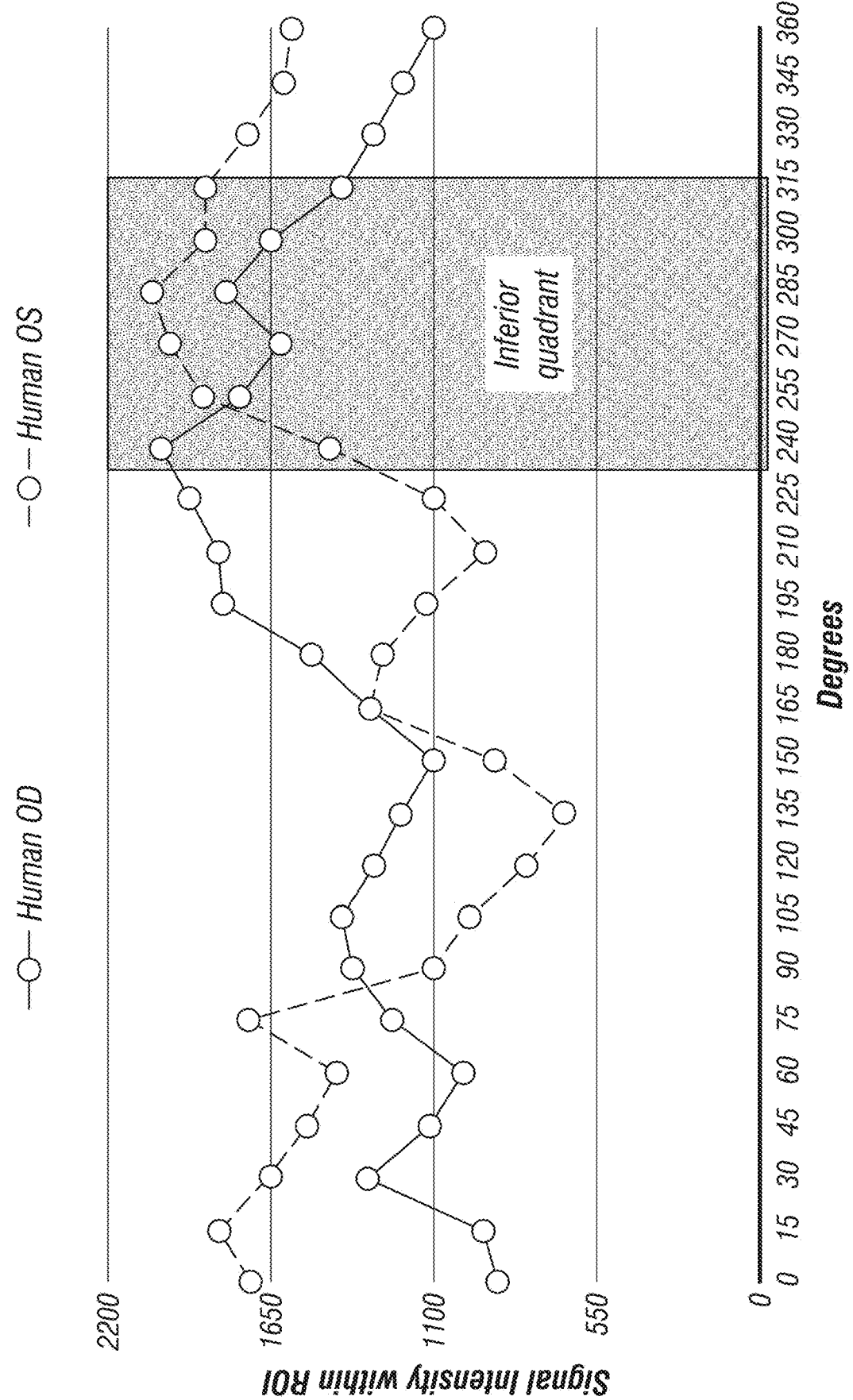
FIG. 8A is a graph showing fluorescent signal intensity distribution along the limbal perimeter.
Figure 8B:
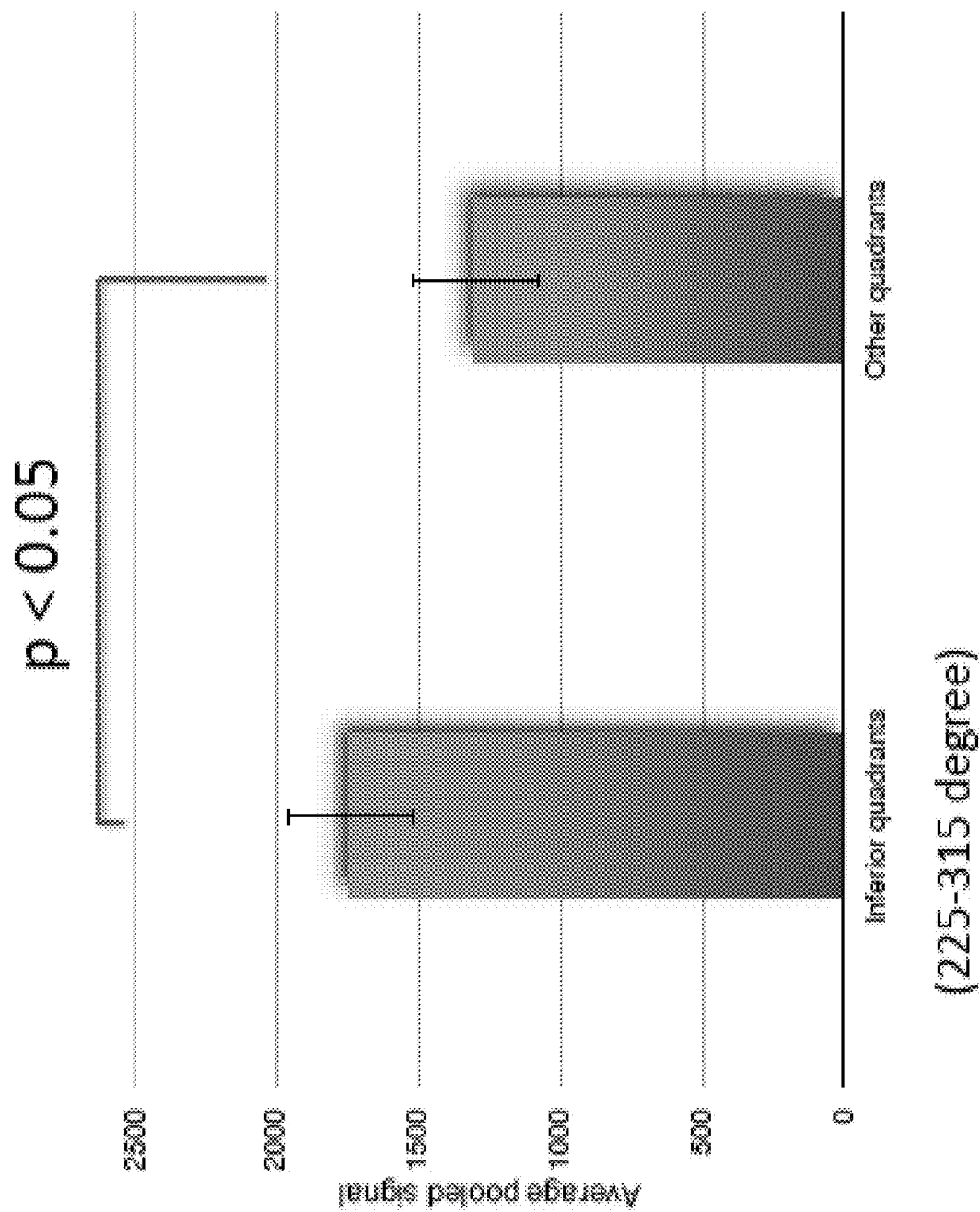
FIG. 8B is a graph showing the amount of fluorescence in the inferior quadrant compared to all other quadrants.

Regional variation in fluorescein intensity along the limbus could be qualitatively appreciated, as shown in FIG. 6A. Representative frames 50 from individual quadrants were chosen to highlight the differences in fluorescence signals along the limbus. The vessel segmentation algorithm was applied to individual frames acquired 15 degree apart along the limbus. The difference can be quantified using the vessel segmentation algorithm, which automatically detects the vessel border 62 and midline 64, as shown in FIGS. 5B and 5C, and quantifies vessel diameter and signal intensity in the chosen region of interest. An example composite image 60 is shown where the vessel border was outlined in blue 62 and the vessel midline in red 64. Vessel diameter distribution along the limbus in human eyes is non-uniform, with larger-diameter episcleral vessels seemingly grouped in clusters that span for 40 to 50 degrees, as shown in the graph of FIG. 7. Fluorescent signal intensity appears to concentrate more in the inferior quadrant in both human eyes, illustrated in the graph of FIG. 8A. In fact, when compared with the other quadrants combined, the inferior quadrant has a statistically higher amount of fluorescence (1742+/−271 vs 1300+/−316, $p<0.05$), as presented in the graph of FIG. 8B.

As demonstrated herein, the confocal laser microendoscope system of the present invention can be used to visualize episcleral vessels in human eyes with minimal tissue manipulation. Further, in the ex vivo system involving a perfused eye, the optimal time to image episcleral vessels is seven minutes after fluorescein injection into the anterior chamber. Still further, episcleral vessel diameter and density can be acquired in real-time and shows that the inferior quadrant of the two human eyes in this study have statistically greater amount of fluorescence compared to the other quadrants.

This study showed that the microendoscope was able to image surface episcleral vessels. The flexibility of the microendoscope catheter also enables the operator to easily rotate the endoscope to image other areas of the lim bus. The microendoscope was not able to visualize Schlemm's canal ab externo because its tissue penetration is only 30 micron. Construction of a scleral flap can assist in visualizing Schlemm's canal, which was confirmed by the tubular structure's dimension (75-100 micron) and its peri-limbal location. However, we were able to maintain the view to Schlemm's canal for only less than ten seconds after fluorescein injection likely because as the eye was actively perfused, fluorescein was egressing the intrascleral vessels along the cut edges of the scleral flap. As demonstrated herein, the ability to image episcleral vessels noninvasively is unique and of great diagnostic value.

The confocal laser microendoscope in this study uses fluorescein to provide contrast. Because the intracameral fluorescein would follow and thereby outline the functioning aqueous veins and episcleral vessels, the diameter and density of the episcleral vessels serve as a surrogate functional marker for flow associated with the limbal area imaged by the microendoscope. As demonstrated herein, a vessel segmentation algorithm can be applied to quantify episcleral vessel morphology; furthermore, vessel diameter and the amount of flow both show regional variation, and that flow is more concentrated in the inferior quadrant in the two human eyes studied. This observation agreed with previous studies showing that the collector channels are more concentrated in the inferior and temporal quadrants in human eyes (McKee et al; and Meyer, P. A., Patterns of blood flow in episcleral vessels studied by low-dose fluorescein videoangiography. Eye (Lond), 1988. 2 (Pt 5): p. 533-46). Moreover, the microendoscope imaged episcleral vessels with little or no tissue manipulation. The microendoscope's flexibility and the foot 16 pedal (FIG. 1) also enhance the operator's maneuverability. Both of these features augment the microendoscope's clinical translatability as the image acquisition can be performed in an ambulatory outpatient setting.

Although fluorescein had shown to be safe for intraocular use on human eyes (Benedikt), indocyanine green can alternatively be used to provide the source of contrast. A laser scanning unit that excites at indocyanine's peak absorption of 600 nm is currently being developed to facilitate this purpose.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for identifying one or more target treatment areas in an eye of a living subject for subsequent performance of a glaucoma surgical treatment, said method comprising:

obtaining or providing an imaging probe system which comprises a laser microendoscope having an intraocular tip, a processor and a feedback device;

introducing a liquid contrast agent into the eye such that the liquid contrast agent flows through episcleral aqueous outflow vessels;

positioning the intraocular tip of the laser microendoscope in contact with the eye;

using the laser microendoscope to image the episcleral aqueous outflow vessels within a plurality of regions of interest as those episcleral aqueous outflow vessels are perfused with the liquid contrast agent;

causing image data to be transmitted from the laser microendoscope to the processor;

causing the processor to quantify flow of the liquid contrast agent through the episcleral aqueous outflow vessels within each of the plurality of regions of interest;

causing the feedback device to indicate differences in flow of the liquid contrast agent through the plurality of regions of interest; and using the differences in flow indicated by said feedback device to identify said one or more target treatment areas for subsequent performance of said glaucoma surgical treatment on the basis of the differences in flow of the liquid contrast agent through the plurality of regions of interest indicated by the feedback device, wherein the laser microendoscope emits, from the intraocular tip, laser energy capable of penetrating through scleral tissue to a penetration depth of 30 microns, wherein the processor is configured to apply a vessel segmentation algorithm to the image data obtained by the laser microendoscope from the plurality of regions of interest of the eye and to quantify flow of liquid contrast agent through episcleral aqueous outflow vessels located within each of the plurality of regions of interest, wherein the feedback device is configured to indicate the differences in flow of the liquid contrast agent through the episcleral aqueous outflow vessels within each of the plurality of region of interest, and wherein said glaucoma surgical treatment comprises at least one of i) ablating or forming an opening in trabecular meshwork tissue and ii) implanting a stent or aqueous drainage facilitating device to facilitate aqueous drainage from the eye.

2. The method of claim 1, wherein the step of using the laser microendoscope to image the episcleral aqueous outflow vessels within said plurality of regions of interest as those episcleral aqueous outflow vessels are perfused with the liquid contrast agent comprises moving the laser microendoscope so as to acquire images at 15 degree intervals along a limbus of the eye.

3. The method of claim 1, wherein the liquid contrast agent fluoresces.

4. The method of claim 3, wherein the liquid contrast agent comprises fluorescein.

5. The method of claim 1, wherein the liquid contrast agent comprises indocyanine green.

6. The method of claim 1, wherein the microendoscope is positioned substantially 1 mm behind a limbus of the eye.

7. The method of claim 1, wherein the step of positioning the intraocular tip of the laser microendoscope in contact with the eye comprises forming a flap incision in the eye and positioning the intraocular tip of the laser microendoscope within the flap incision.

8. The method of claim 1, wherein the step of using the laser microendoscope to image the episcleral aqueous outflow vessels within said plurality of regions of interest as those episcleral aqueous outflow vessels are perfused with the liquid contrast agent is performed about 7 minutes after the step of introducing the liquid contrast agent into the eye such that the liquid contrast agent will outflow through the episcleral aqueous outflow vessels of the eye.

9. The method of claim 1, wherein the feedback device comprises a visual display which indicates variations in outflow through the episcleral aqueous outflow vessels within the plurality of regions of interest by displaying a composite image of each of the plurality of regions of interest, wherein the composite image includes a first indicator representing a centerline of each of the episcleral aqueous outflow vessel and a second indicator representing a border of each of the episcleral aqueous outflow vessel.

10. The method of claim 1 further comprising causing said glaucoma surgical treatment to be performed at the one or more target treatment areas identified on the basis of differences in flow of the liquid contrast agent through the plurality of regions of interest.

11. The method of claim 1 wherein the laser microendoscope is held stationary while imaging the episcleral aqueous outflow vessels within said plurality of regions of interest as those episcleral aqueous outflow vessels are perfused with the liquid contrast agent.

12. The method of claim 1 wherein the microendoscope is positioned between 0 and 3 millimeters behind a limbus of the eye.

* * * * *